United States Patent [19]

Vermaak

[11] Patent Number: 5,522,397
[45] Date of Patent: Jun. 4, 1996

[54] METHOD OF AND APPARATUS FOR MONITORING LUNG FUNCTION

[76] Inventor: Jan C. Vermaak, 8 Runkel Drive, Somerset West, Cape Province, South Africa

[21] Appl. No.: 208,024

[22] Filed: Mar. 8, 1994

[30] Foreign Application Priority Data

Mar. 10, 1993 [ZA] South Africa ............................ 97/1716

[51] Int. Cl.⁶ ..................................................... A61B 5/08
[52] U.S. Cl. ........................... 128/720; 128/716; 128/721; 128/725
[58] Field of Search ................................... 128/716, 719, 128/720, 721, 725

[56] References Cited

U.S. PATENT DOCUMENTS

| | | |
|---|---|---|
| 3,857,385 | 12/1974 | Hampl . |
| 4,036,222 | 7/1977 | Gillard et al. ........................... 128/720 |
| 4,220,161 | 9/1980 | Berlin et al. . |
| 4,856,532 | 8/1989 | Johnson . |
| 5,060,655 | 10/1991 | Rudolph . |
| 5,233,998 | 8/1995 | Chowienczyk et al. ................. 128/720 |

FOREIGN PATENT DOCUMENTS

| | | |
|---|---|---|
| 2016073 | 10/1971 | Denmark . |
| 2034097 | 1/1972 | Denmark . |
| 0437055 | 7/1991 | European Pat. Off. . |
| 1029526 | 12/1958 | Germany . |
| 1097269 | 6/1984 | U.S.S.R. . |
| 2077444 | 12/1981 | United Kingdom . |
| WO92/20393 | 11/1992 | WIPO . |

*Primary Examiner*—Angela D. Sykes
*Assistant Examiner*—Stephen Huang
*Attorney, Agent, or Firm*—Harris, Tucker & Hardin

[57] ABSTRACT

A method of measuring lung function in a subject includes connecting a pneumotach in series with the subject's airway and taking pressure readings upstream and downstream of a fixed resistance element in the pneumotach. Second pressure readings are taken with a second resistance element in place, and the sets of readings are processed to calculate characteristic flow curves for the subject's airway. First and second time constants are calculated from the flow curves, and are used to calculate values of lung compliance and airway resistance. The invention extends to a pneumotach device with a fixed first resistance element and a removable second resistance element. The invention also extends to apparatus for monitoring lung function including the pneumotach device, together with a pair of pressure sensors and a processor circuit for carrying out the necessary calculations of the time constants, and the lung compliance and airway resistance values. A display is provided for giving an indication of the calculated values.

13 Claims, 16 Drawing Sheets

5,522,397

1

METHOD OF AND APPARATUS FOR MONITORING LUNG FUNCTION

BACKGROUND OF THE INVENTION

This invention relates to a method of measuring lung function in a subject and to apparatus for use in carrying out the measurement.

The measurement of lung function in humans and other animals has various applications. In patients with emphysema or other respiratory tract diseases, the monitoring of lung function may be useful both in treating the disease and carrying out research. It is also useful to monitor lung capacity and function in sportsmen and women. Various other applications for such measurements exist.

Two significant parameters in measuring lung function are airway resistance ($R_{aw}$) and compliance of the lung and thorax ($C_{lt}$). These parameters are analogous to electrical resistance and capacitance, and define a time constant $\tau = R_{aw} \times C_{lt}$. Previously, airway resistance has been measured by the use of a body plethysmograph, while compliance of the lung and thorax has been measured by the use of a swallowed balloon. This is clearly a cumbersome and awkward procedure.

It is an object of the invention to provide an alternative method of and apparatus for measuring lung function.

SUMMARY OF THE INVENTION

According to the invention a method of monitoring lung function in a subject comprises the steps of:

connecting a pneumotach in series with the subject's airway;

taking first airway pressure readings upstream and downstream of a first resistance element in the pneumotach;

inserting or removing a second resistance element in the pneumotach so that the total resistance in the subject's airway is changed;

taking second airway pressure readings upstream and downstream of the first resistance element in the pneumotach;

processing the first and second pressure readings to calculate respective first and second characteristic flow curves for the subject's airway;

deriving first and second time constants from the first and second flow curves; and calculating values of lung compliance and airway resistance for the subject from the first and second time constants.

Preferably, a plurality of first and second airway pressure readings are taken for calculation of the respective first and second airway flow curves.

The airway flow curves are preferably curves of air flow against time, from which the lung time constants can be derived.

Further according to the invention pneumotach apparatus for monitoring lung function in a subject comprises:

a body defining a conduit therein for connection in series with the subject's airway;

a first resistance element in the conduit;

first and second ports in the body in communication with the conduit on either side of the first resistance element; and

2 a second resistance element movable between an operative position in the conduit in which it increases the resistance to gas flow in the conduit, and an inoperative position in which it does not substantially affect gas flow in the conduit.

The first and second resistance elements may be perforated plates with a predetermined effective aperture size.

The second resistance element is preferably adapted to be removed from the body in its inoperative position. For example, the second resistance element may be housed releasably in a slot in the body which intersects the conduit.

The ports in the body may be adapted for connection to respective pressure sensors via pipes or tubes.

Alternatively, the body may be adapted to house pressure sensors in or adjacent to the ports.

In either case, the pressure sensors are arranged to measure the pressure differential across the first resistance element, from which measurement the air flow in the conduit can be calculated.

The invention extends to apparatus for monitoring lung function in a subject comprising pneumotach apparatus as defined above, and further comprising:

first and second pressure sensors in communication with the first and second ports in the body and arranged to generate respective output signals corresponding to respective pressure readings; and processing means for receiving first and second sets of output signals from the sensors, corresponding to pressure readings with the second resistance means in the inoperative and operative positions; for calculating first and second characteristic flow curves for the subject's airway; for deriving first and second time constants from the first and second flow curves; and for calculating values of lung compliance and airway resistance therefrom.

The apparatus may further include indicator means such as a digital or graphic display for displaying one or more of the measured or calculated values.

The processing means may include respective amplifiers for amplifying the outputs of the first and second pressure sensors, at least one analogue to digital converter for converting the amplified output signals into a digital form, and a microprocessor for carrying out the required calculations and for generating output or display signals as required.

DESCRIPTION OF AN EMBODIMENT

Figure 1:
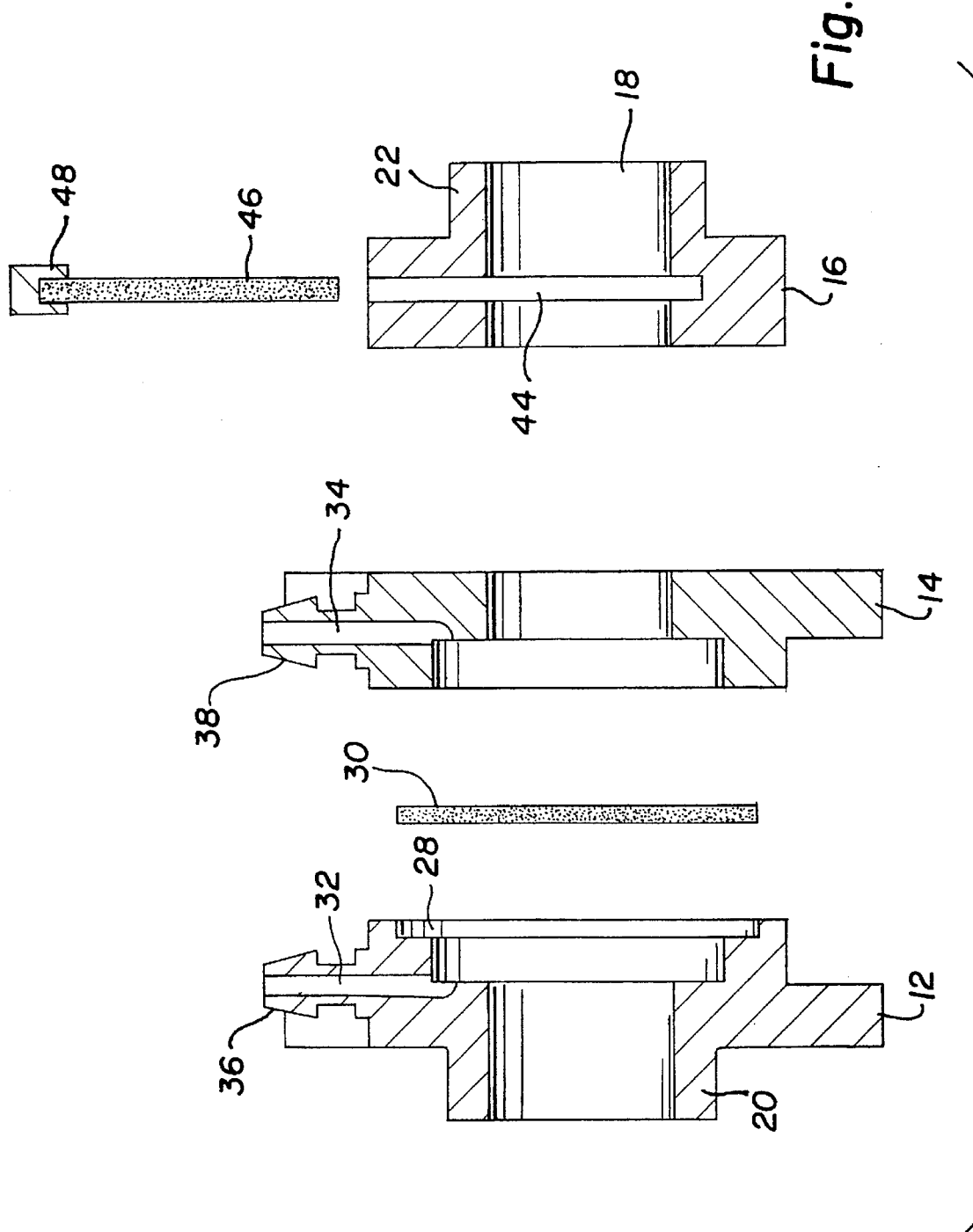
FIG. 1 is an exploded sectional side view of pneumotach apparatus according to the invention.
Figure 2:
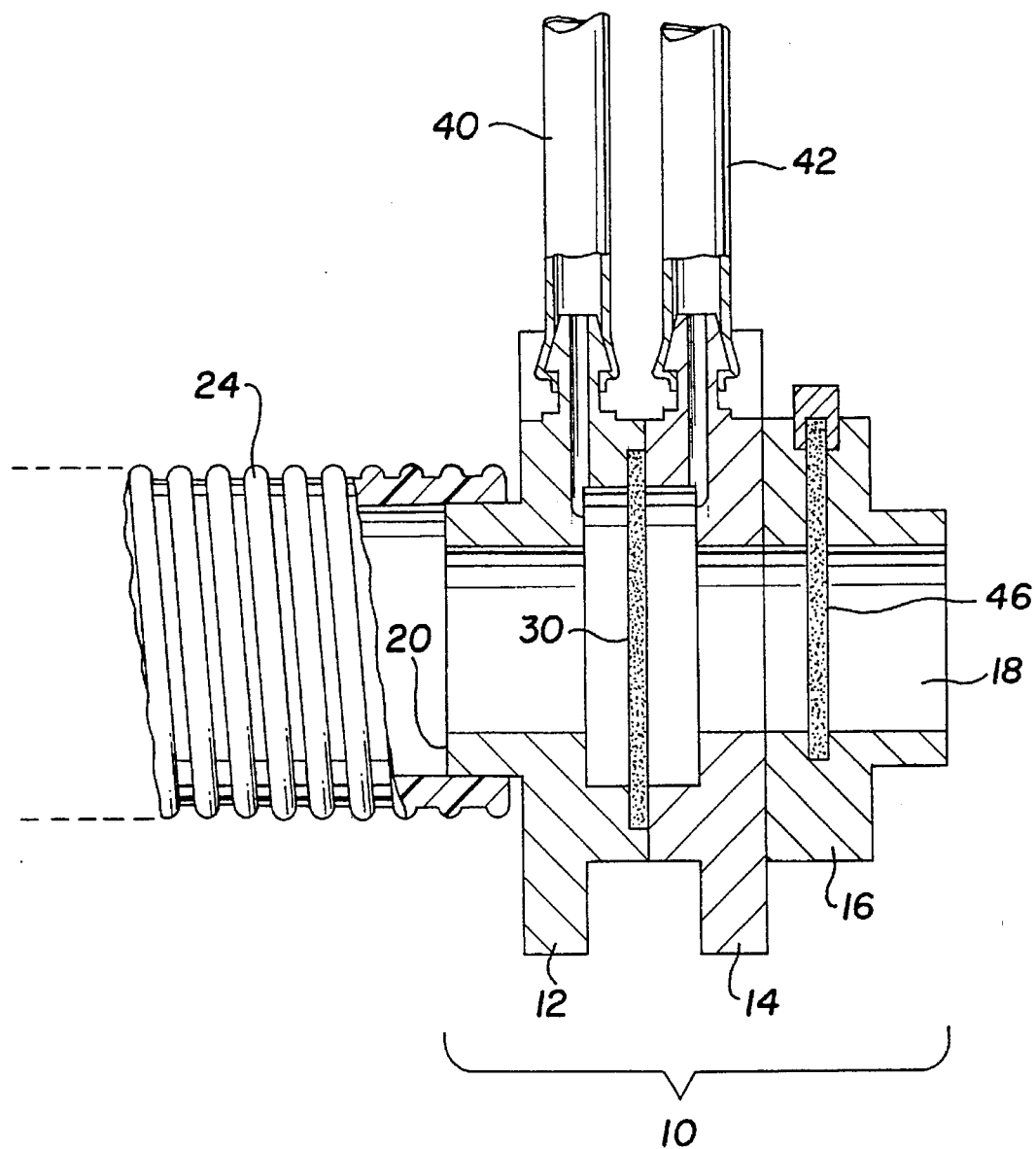
FIG. 2 is a partial sectional side view of the apparatus of FIG. 1 in an assembled condition.

The apparatus illustrated in FIGS. 1 and 2 of the drawings is a modified pneumotach which is adapted for insertion in series with the airway of a subject, and which enables two different predetermined resistance elements to be placed in series with the subject's airway, to enable accurate measurements to be made from which lung function information can be calculated.

The pneumotach has a body 10 comprising an inlet portion 12, a central portion 14 and an outlet portion 16 which are generally circular in plan and which each have a circular central aperture so that the body as a whole defines a central tubular conduit 18. The inlet portion 12 and the outlet portion 16 of the body 10 have respective tubular ends 20 and 22 for connection of pipes or hoses to the pneumotach. In FIG. 2, a flexible hose 24 is connected to the inlet portion 12, and is shown (in FIG. 3) inserted into the mouth of a human subject 26. Typically, the pneumotach 10 will form part of an anaesthetic circuit or a more complex measurement arrangement than that illustrated schematically in FIG. 3.

Referring again to FIGS. 1 and 2, the inlet portion 12 of the body 10 defines a circular seat 28 concentric with its bore which receives a resistance element in the form of a perforated plate 30. The plate 30 typically comprises a metallic disc with perforations of a predetermined number and size therein, so that it provides a predetermined degree of resistance to air or gas flow through the conduit 18 of the pneumotach. The resistance element 30 is clamped in position in the seat 28 when the inlet portion and the central portion 14 of the pneumotach are fastened together, as shown in FIG. 2.

Ports 32 and 34 are formed in the inlet portion 12 and the central portion 14 of the body, respectively, and terminate in spigots 36 and 38 which have enlarged heads for retaining flexible tubes 40 and 42. The ports 32 and 34 extend radially through the body portions 12 and 14 into communication with the central conduit 18.

The outlet portion 16 of the pneumotach body is formed with a radially extending slot 44 therein, which intersects the conduit 18. This slot receives a second resistance element 46 which is similar to the resistance element 30 but which has a tab 48 or other gripping means at one edge thereof, to allow it to be grasped by a user of the apparatus and to be inserted into or removed from the slot 44. In FIG. 2, the second resistance element 46 is shown in position in the slot 44, so that the first and second resistance elements are effectively placed in series with the subjects' airway. When the second resistance element 46 is removed from the slot 44, only the first resistance element 30 remains in the patient's airway, so that it can be seen that the total resistance inserted in the subject's airway can be varied between a value $R_1$ corresponding to the first resistance element 30 only, and a second value $R_1+R_2$, corresponding to both resistance elements 30 and 46.

In a prototype of the invention, the resistance element 30 had a resistance value of about 0.35 cm $H_2O$ per liter per second, while the value of the resistance element 46 was about 1.0 cm $H_2O$ per liter per second.

Figure 3:
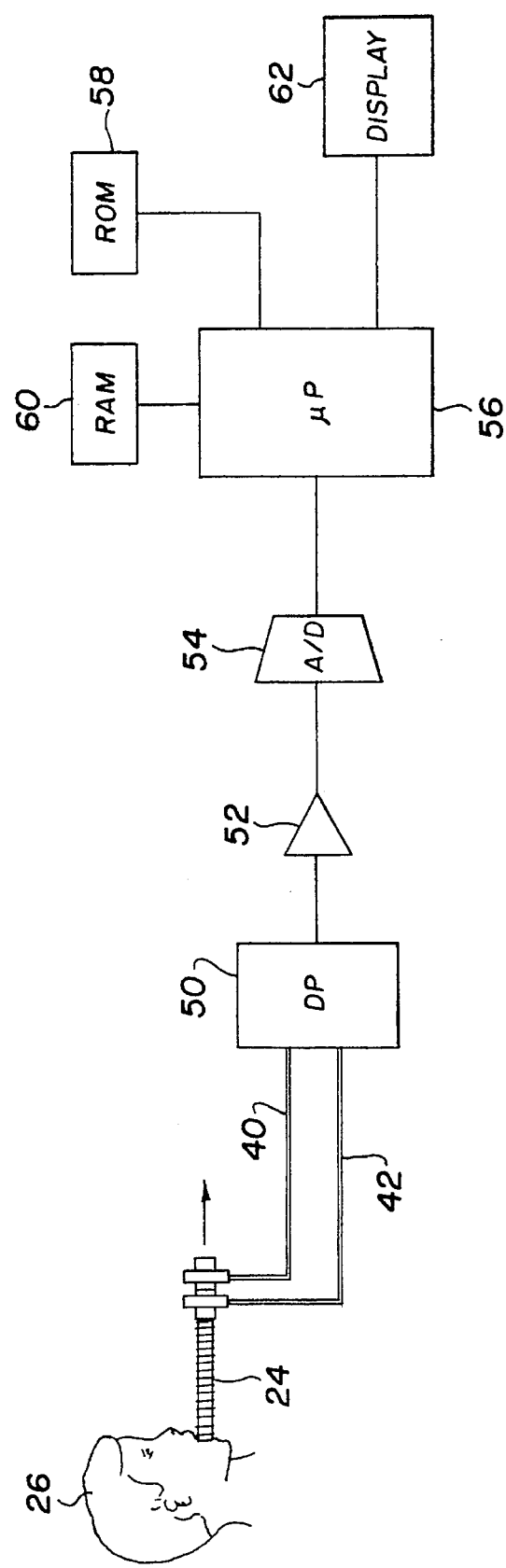
FIG. 3 is a simplified schematic block diagram of apparatus for measuring lung function incorporating the pneumotach of FIGS. 1 and 2.

Referring now to FIG. 3, the tubes 40 and 42 connected to the pneumotach of FIGS. 1 and 2 are shown connected to a differential pressure transducer 50. The pressure transducer provides electrical output signals which are proportional to the pressure difference across the first resistance element 30 in the conduit 18 of the pneumotach. The output of the pressure transducer 50 is amplified by a pre-amplifier 52, and the amplified output signal is fed to an analogue to digital (A/D) converter 54. The A/D converter digitises the amplified output signal from the pressure transducer, and the digital output signal is fed to a microprocessor 56 with associated read only memory (ROM) 58 and random access memory (RAM) 60. A digital display 62 (or another display such as a graphic display) is arranged to be driven by an output of the microprocessor 56 or an associated display driver.

Figure 7:
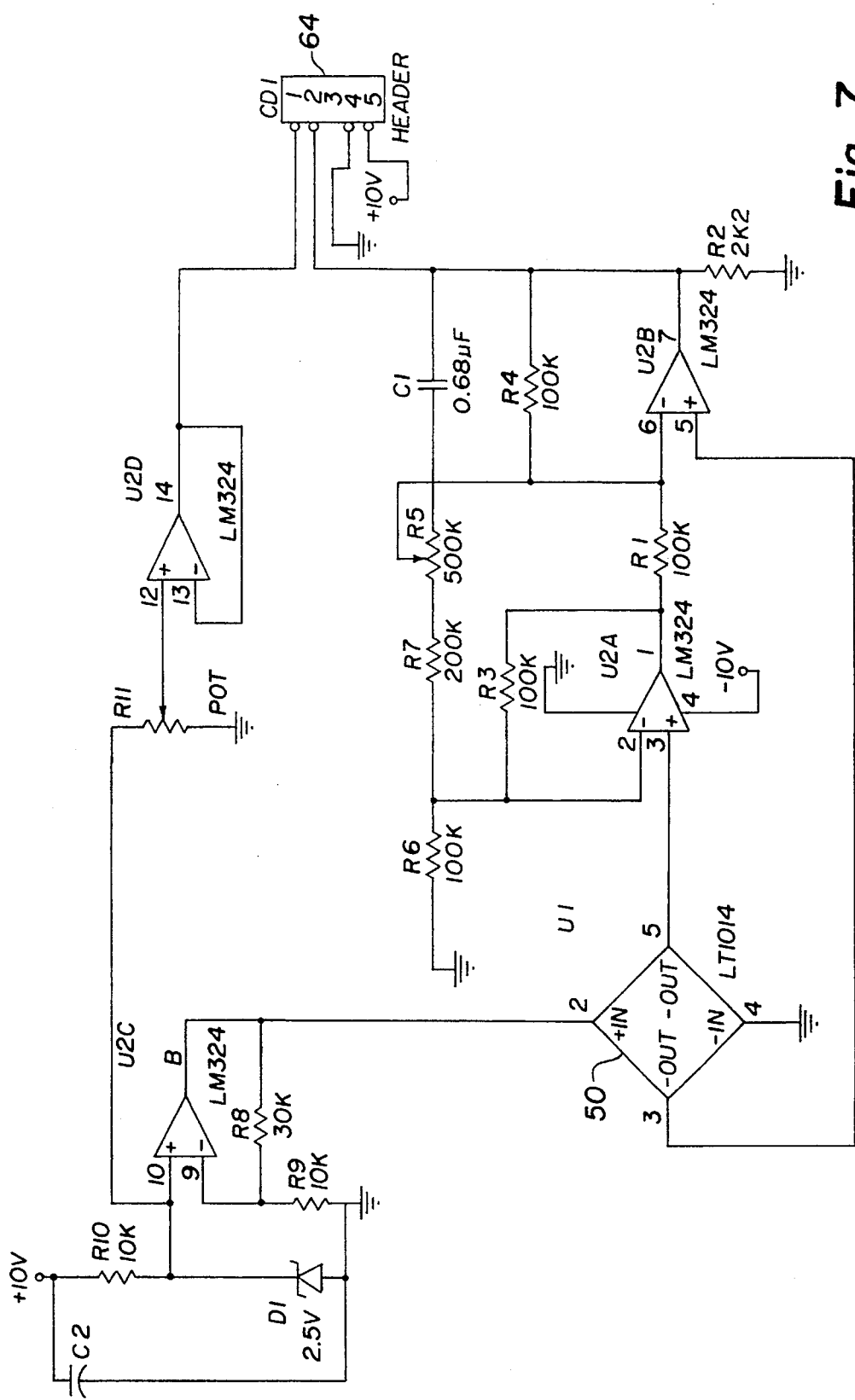
FIG. 7 is a schematic circuit diagram of a preamplifier circuit of the apparatus.
Figure 8A:
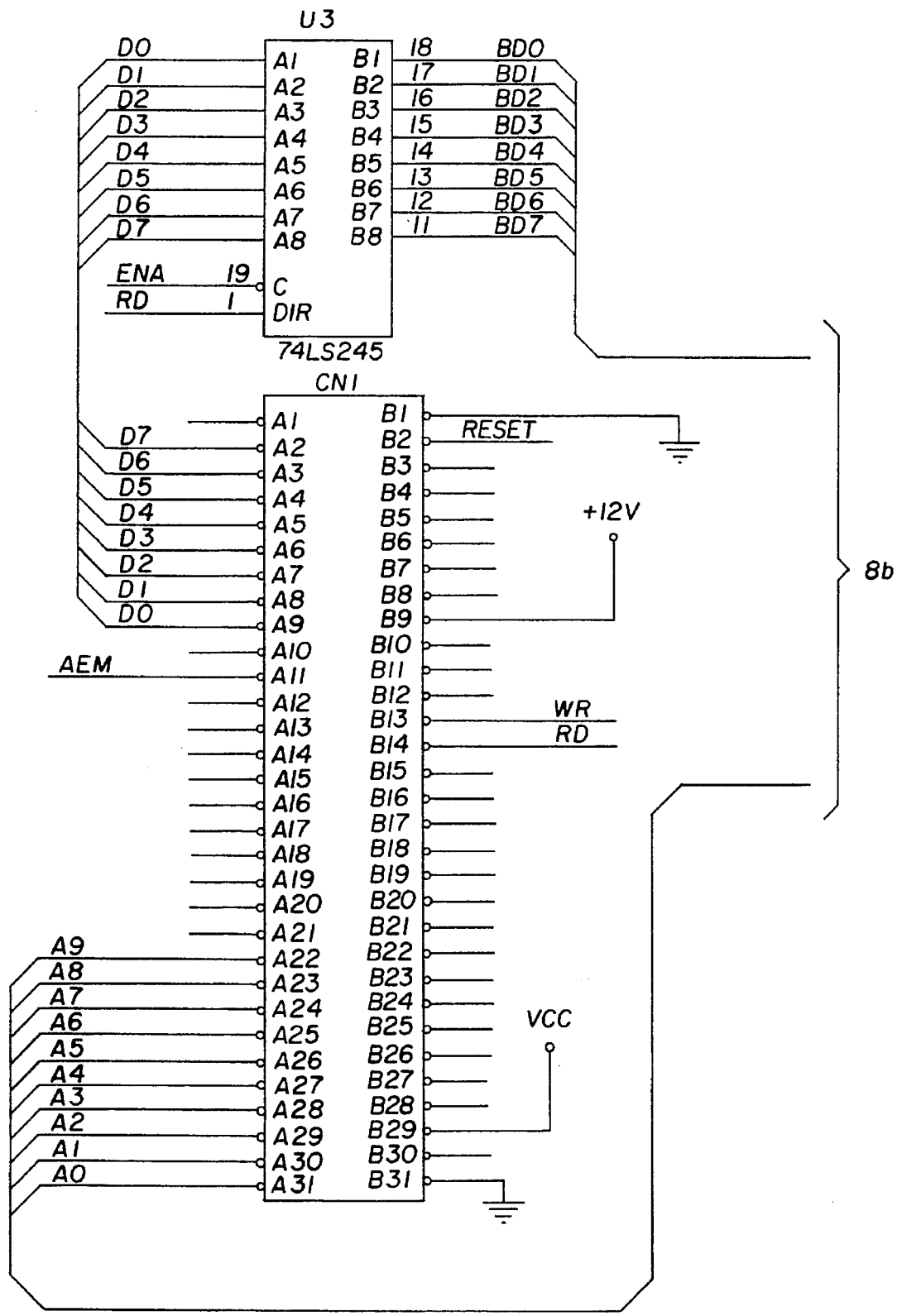
FIG. 8 is a schematic circuit diagram of microprocessor and A/D circuitry of the apparatus.
Figure 8B:
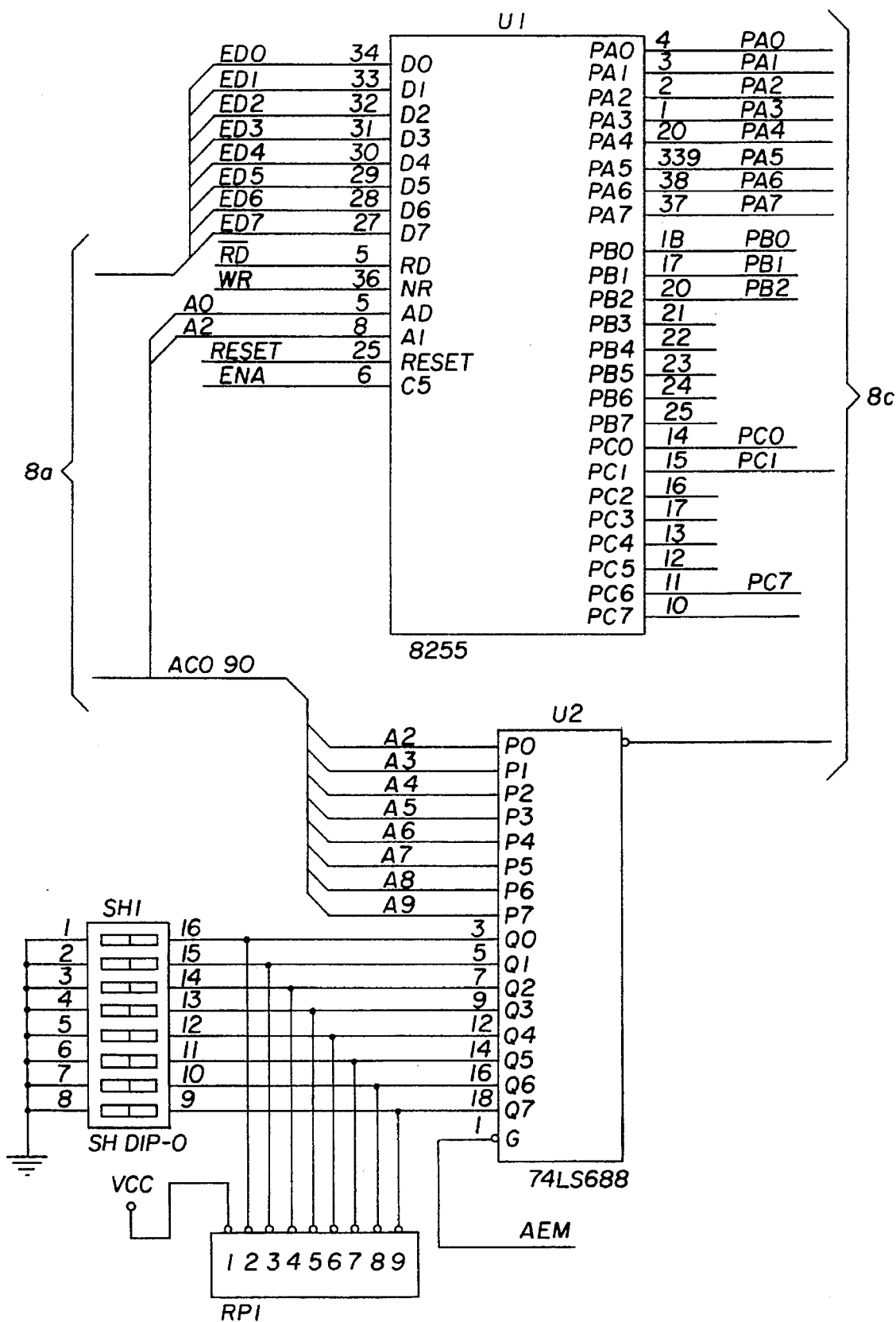
Figure 8C:
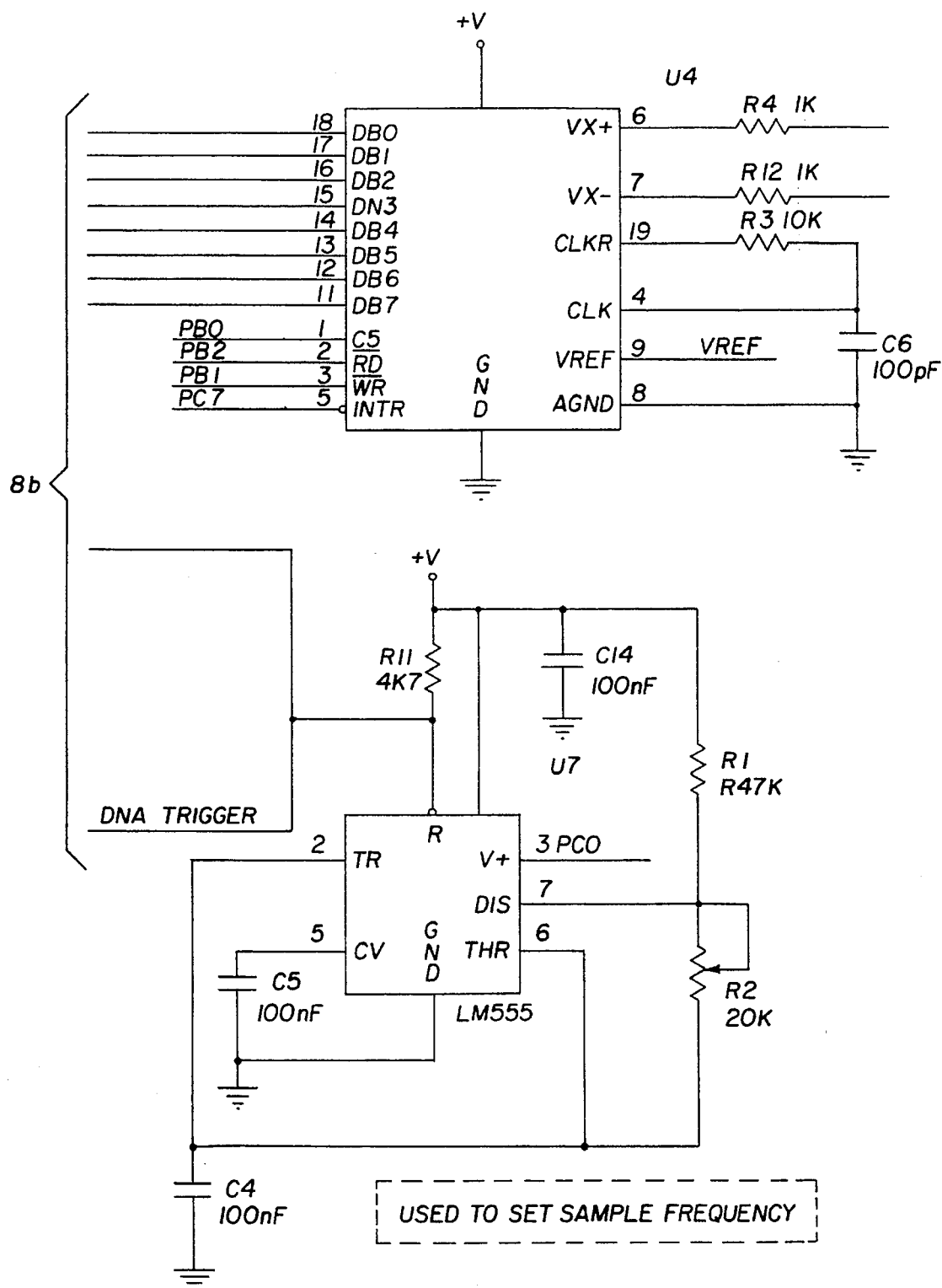
Figure 9:
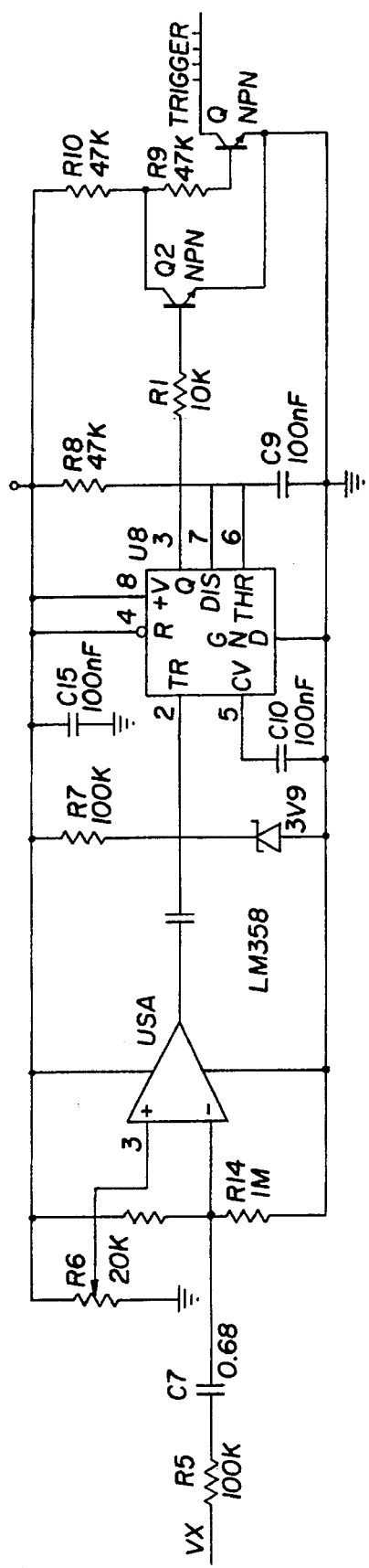
FIG. 9 is a schematic circuit diagram of a trigger and timing circuit of the apparatus.

The electronic circuitry of FIG. 3 is illustrated in greater detail in FIGS. 7, 8 and 9, which are schematic circuit diagrams of circuitry used in the prototype of the invention.

In FIG. 7, the differential pressure transducer 50 is a type LT1014 device, which is connected to respective pairs of LM 324 opamps U2A, U2B, U2C and U2D, which correspond to the preamplifier 52 in FIG. 3. The respective amplified output signals from the preamplifiers are fed to pins 1 and 2 of a connector 64, which is also used to feed power from a power supply circuit to the pressure sensor and the amplifiers. The circuit of FIG. 9 includes a threshold detector U5A which receives the output of the preamplifier circuit of FIG. 7 via a differentiator circuit comprising a resistor R5 and a capacitor C7. The output of the differentiator circuit is a fast rising initial flow signal which is shaped and inverted by the threshold detector U5A and fed to the trigger input of a type 555 timer circuit U8. This starts the timer circuit, which times a 5 second delay, which is chosen to correspond to the maximum likely expiratory time to be measured.

The output of the timer circuit is a positive square pulse which is applied to the base of a transistor Q2. The transistor Q2 is turned on, turning off a second transistor Q1, and generating a 5 second trigger signal.

The trigger signal is used by the circuit of FIG. 8 to trigger a further oscillator circuit based around a type 555 timer U7, which is configured to run at 200 Hz. The trigger signal also triggers a microprocessor U1 which enables an A/D converter U4 and stores the digital data output from the A/D converter in RAM.

Figure 4:
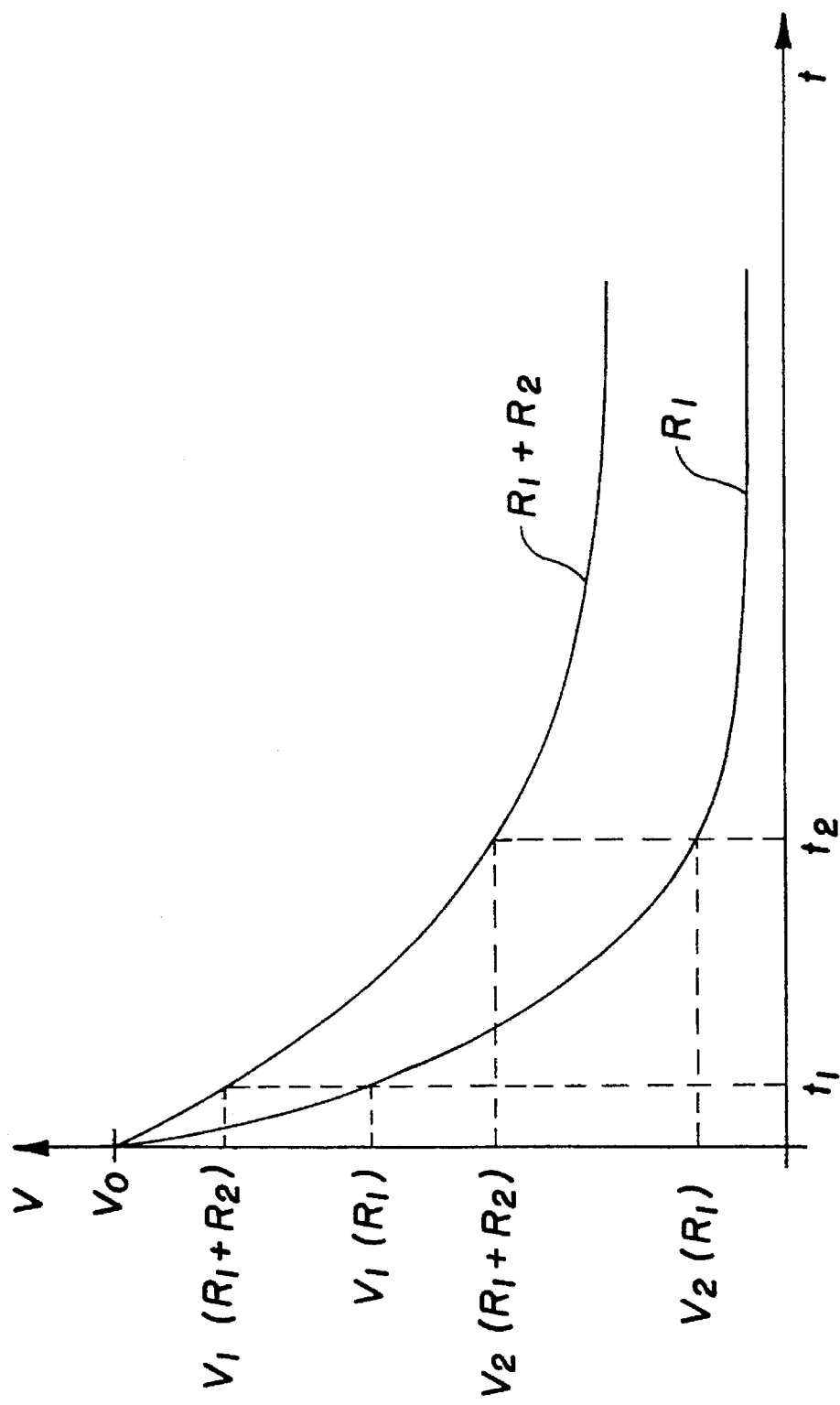
FIG. 4 is a simplified graph illustrating the calculation of relevant parameters by the apparatus of FIG. 3.

FIG. 4 is a graph showing two characteristic flow curves for a subject's airway. It will be seen that the curves have a generally logarithmic decay from an initial volume $V_0$ to a smaller volume which varies with time as the subject exhales. In the uppermost curve, the rate of airflow in the subject's airway is reduced due to the presence of the second resistance element $R_2$, while the lowermost curve shows a more rapid exhalation flow due to the absence of the second resistance element $R_2$.

When the pneumotach apparatus is connected in series with the airway of the subject, a flow of air through the pneumotach due to exhalation results in a pressure differential across the first resistance element 30, and the output signal of the pressure transducer 50, corresponding to this pressure differential, is indicative of the air flow through the pneumatic.

The microprocessor 56 of FIG. 3 operates under the control of software stored in the RAM 58, in accordance with the simplified flow chart of FIG. 6. The apparatus has two basic modes of operation, a "passive expiration" mode and a "forced expiration" mode. Dealing first with the passive expiration mode, the pressure readings of the pressure transducers 44 and 46 are continually converted to digital values and fed to the microprocessor, which stores the values from each transducer, over a period of time of a few seconds, in a data array. This effectively stores the upper and lower curves illustrated in FIG. 4. In each case, a starting time $t_1$ is determined, which corresponds to $0.9 \times V_0$. A second time $t_2$ is calculated so that the difference $t_2-t_1=\tau$. The lung time constant $\tau$ is the time required (in seconds) for the value of V in the graph of FIG. 4 to fall to 1/e or 36.8% of its initial value.

The relationship can be expressed as follows:

$$\tau = \frac{t_2 - t_1}{L \log V_1 - L \log V_2}$$

From the known relationship:

$$\tau = R_{aw} C_{lt}$$

and from the two sets of readings taken with and without the second resistance element in place in the pneumotach, the airway resistance $R_{aw}$ and the compliance of the lung and thorax $C_{lt}$ can be calculated.

Figure 5:
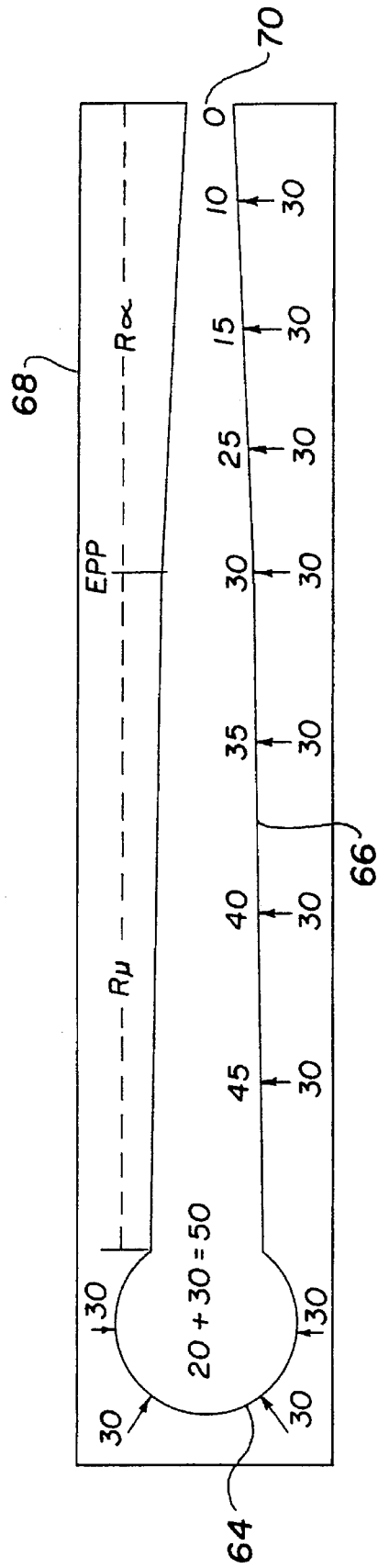
FIG. 5 is a schematic diagram illustrating airway parameters relevant to forced expiration.
Figure 6A:
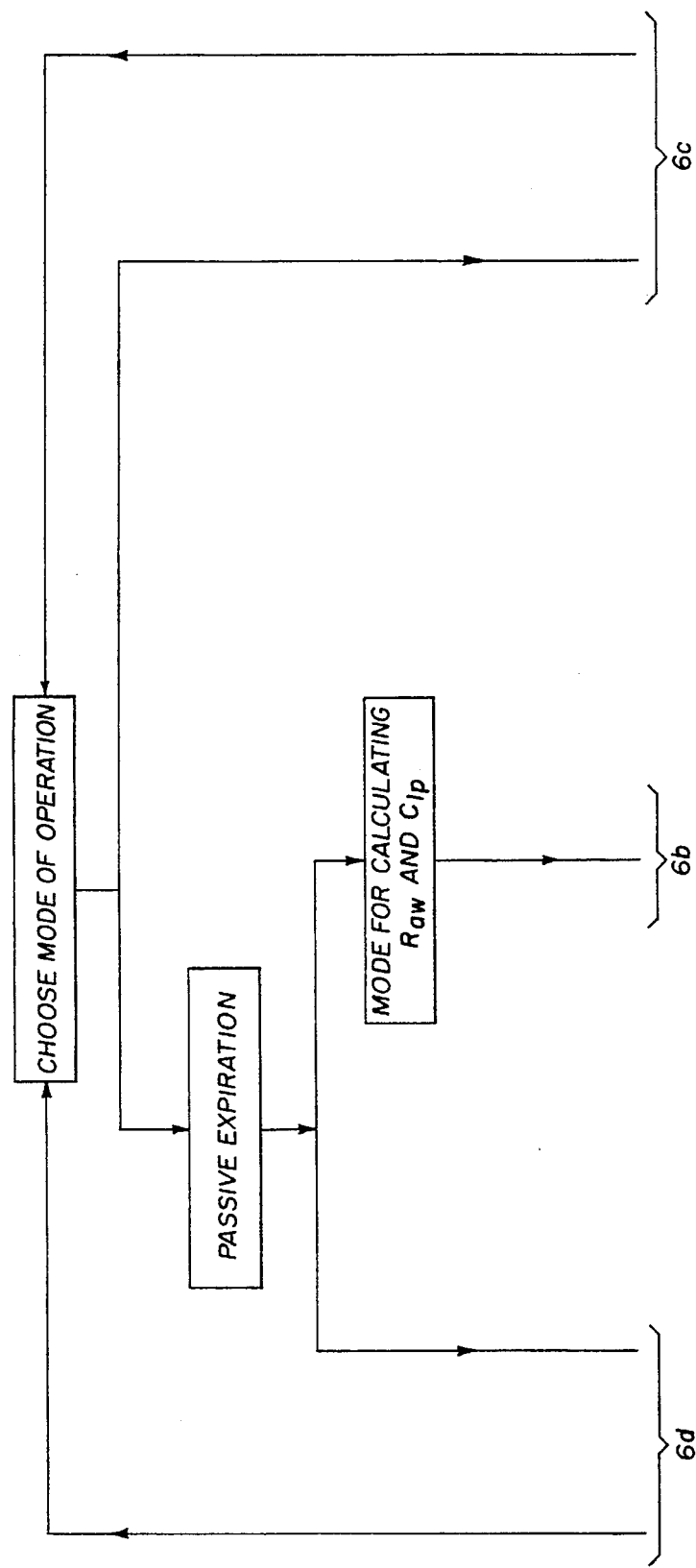
FIG. 6 is a simplified flow chart illustrating the operation of processing means of the apparatus of FIG. 3.
Figure 6B:
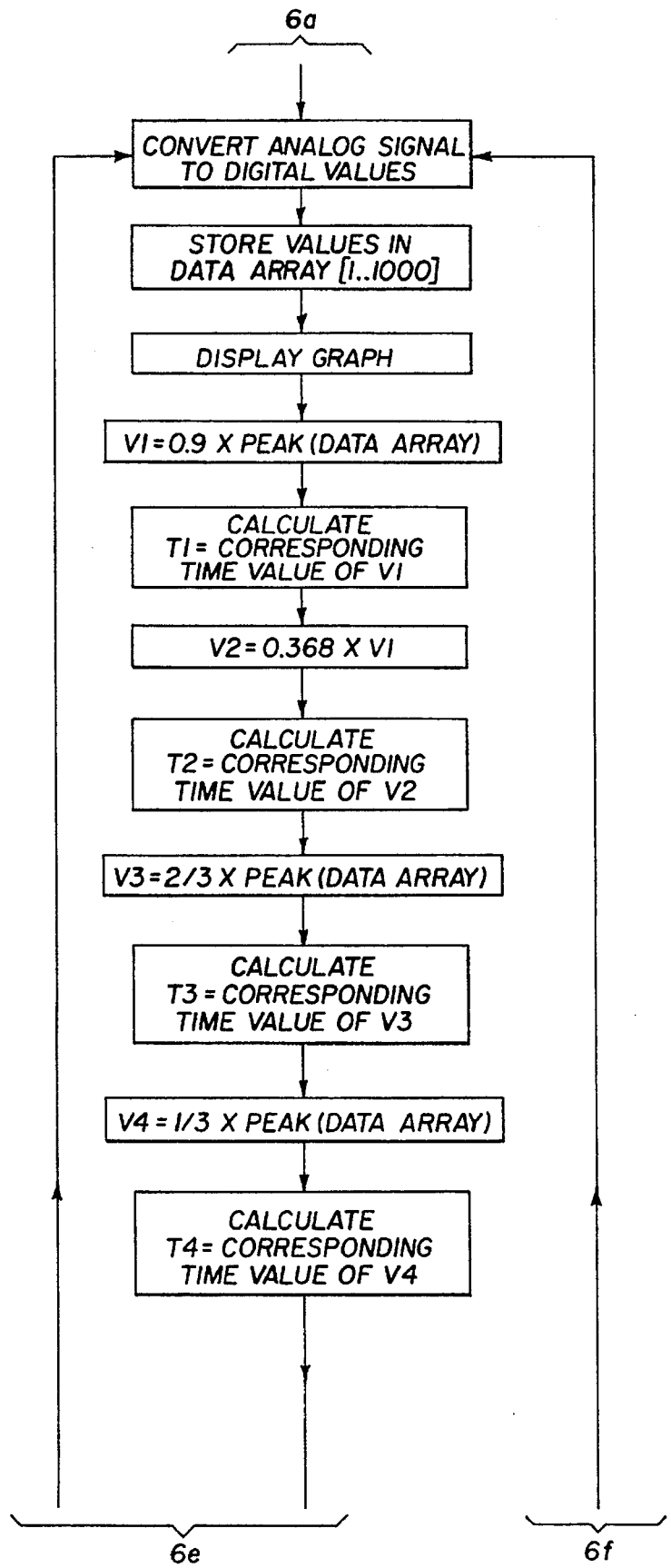
Figure 6C:
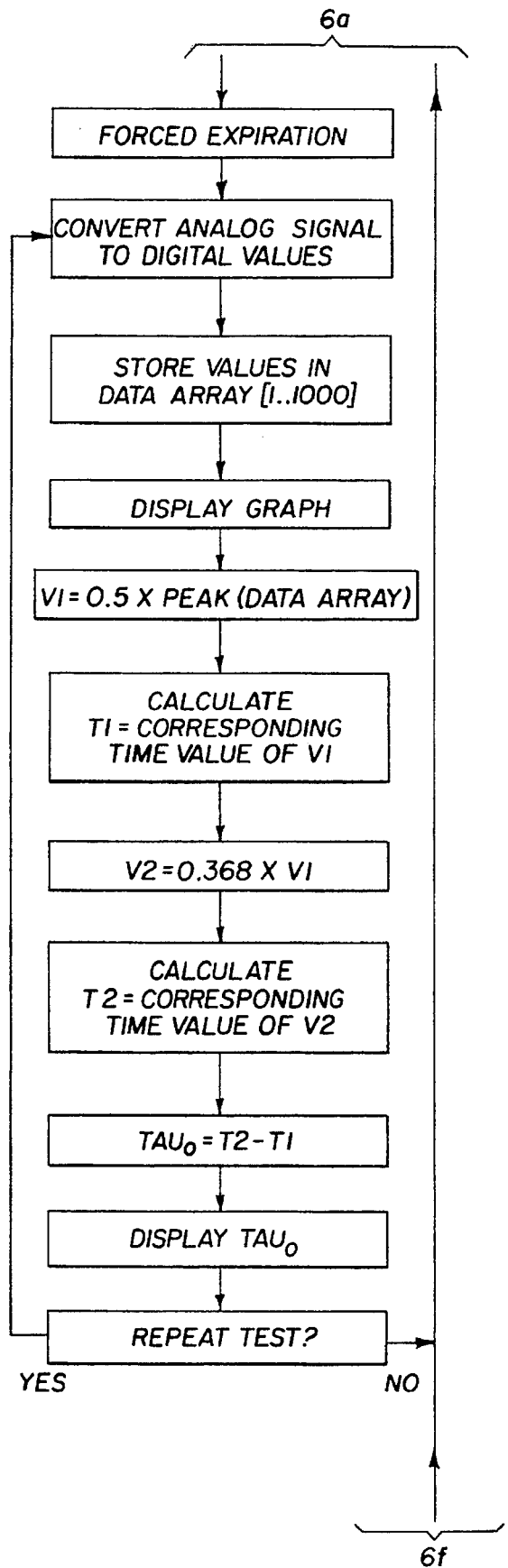
Figure 6D:
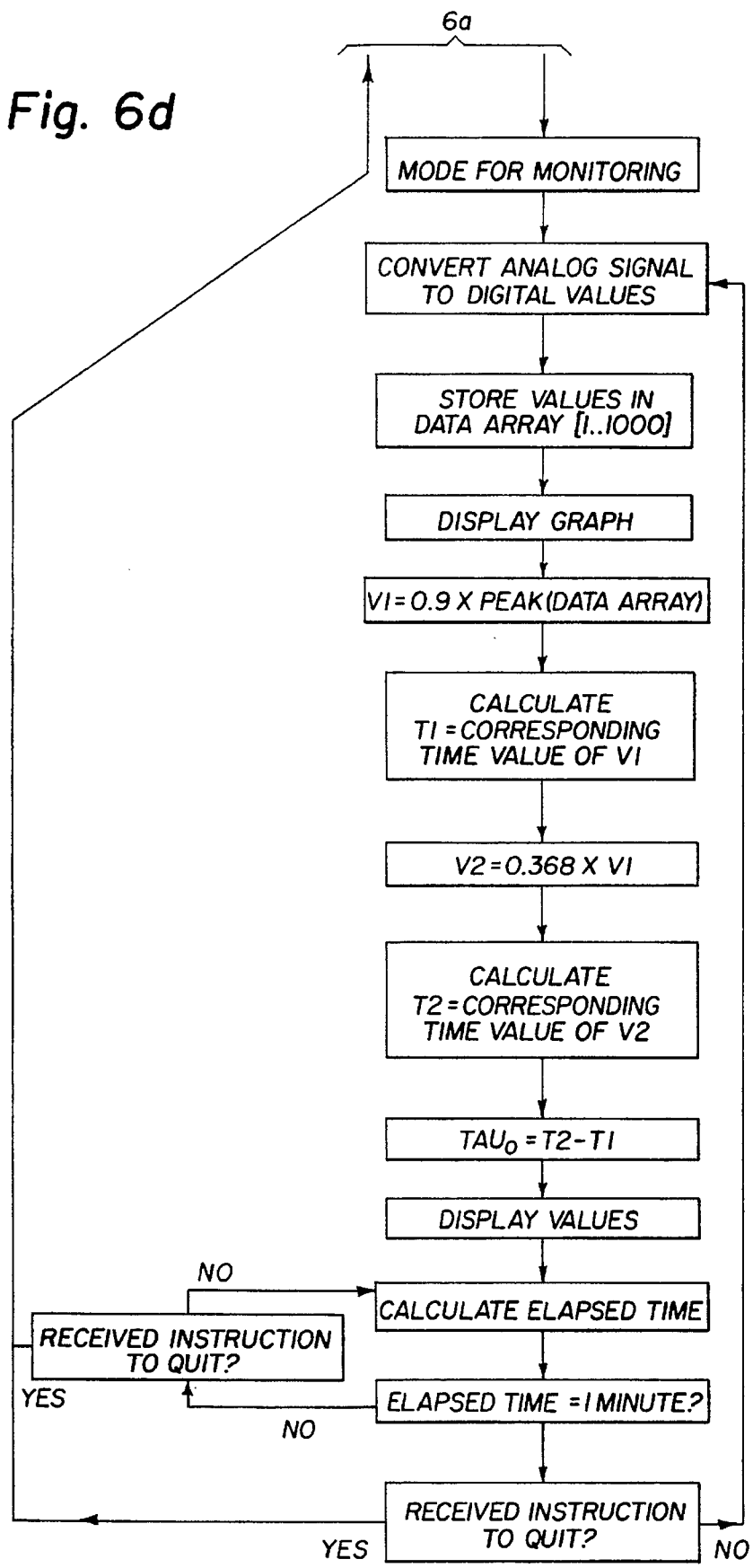
Figure 6E:
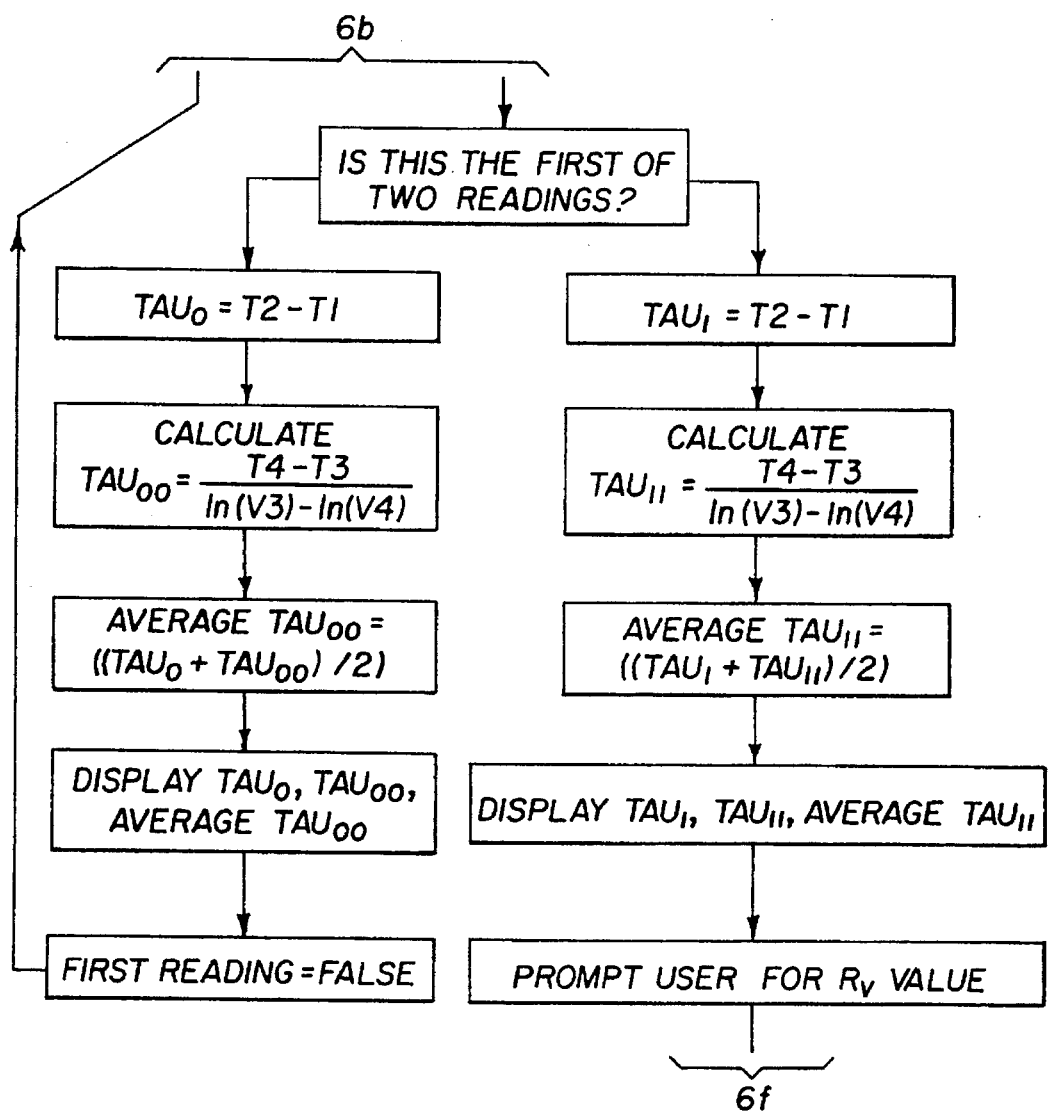
Figure 6F:
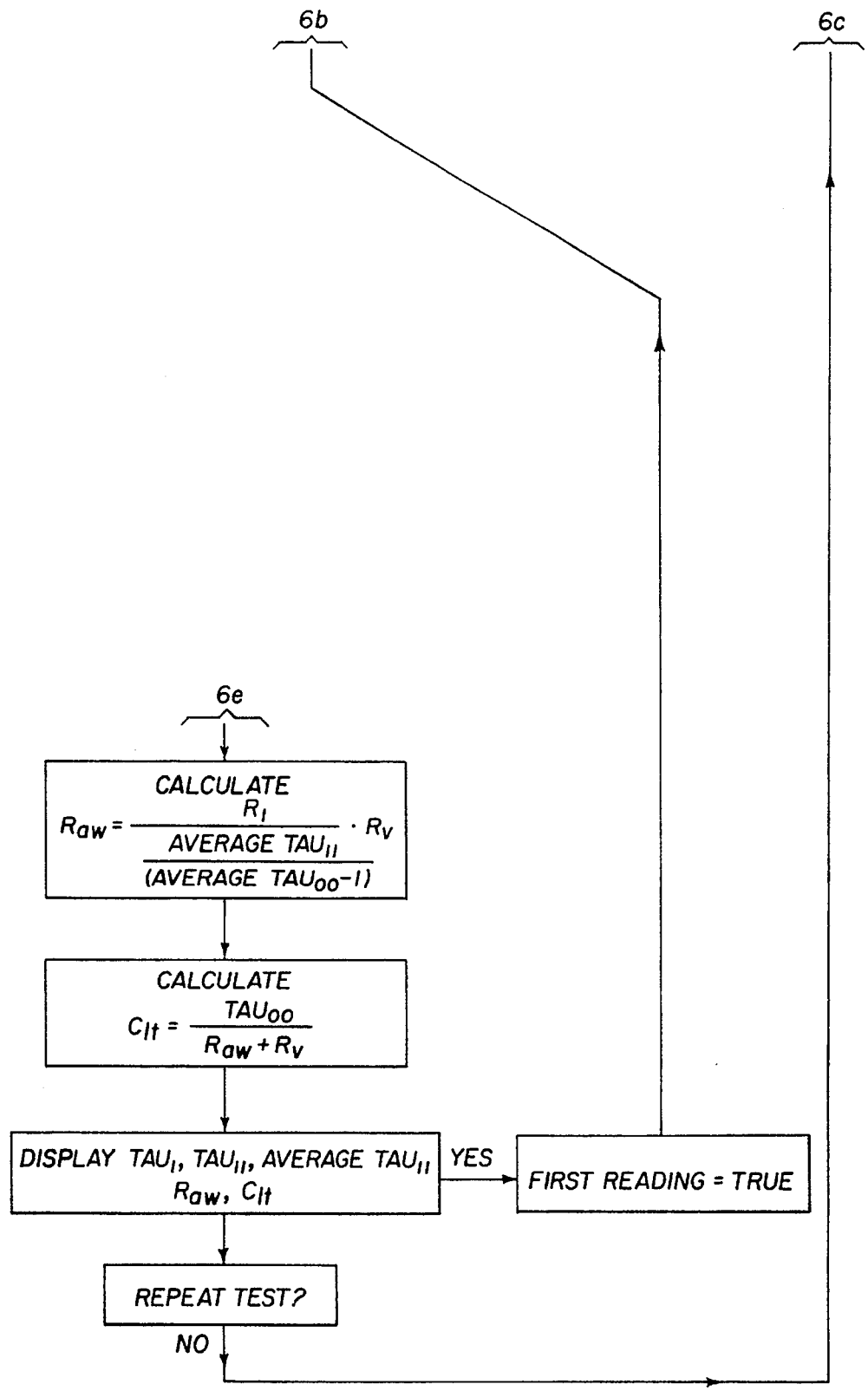

The apparatus of FIG. 3 can also be used in a forced expiration mode. The schematic diagram of FIG. 5 provides an indication of the airway parameters which are relevant in the forced expiration mode. In FIG. 5, the round section 64 at the left of the diagram represents the alveolar sacs of the lung, which combine to form the elastic element or compliance of the lung which in turn is responsible for an increasing recoil of the alveoli as lung volume is increased. The narrow tubular section 66 to the right of the round section 64 represents the conducting airway, while the rectangular box 68 represents the thoracic cage. The opening 70 at the right end of the box 68 represents the opening of the mouth.

Pressure inside the thoracic cage is transmitted to the outside of the alveoli. During exhalation, the pressure in the alveoli is highest because the recoil pressure of the alveoli is added to the intra-thoracic pressure. As the pressure at the mouth is nominally zero, a pressure gradient results as airflow begins.

Somewhere along the conducting airway 66 the pressure inside and outside the airway will be the same. This is the equal pressure point (EPP) indicated in the diagram. The airway upstream of this point is never compressed and is called the upstream segment $R_u$, while the downstream segment is designated $R_d$. The relative lengths of the upstream and downstream segments vary according to the intra-thoracic pressure, but have a fixed relationship when airflow becomes effort independent. During a forced expiration there is an intra-thoracic rise in pressure and a decrease in lung volume as flow begins. As the flow falls, the flow curve becomes divided into an effort dependent first part and an effort independent second part where flow rate cannot be increased by increased intra-thoracic pressure. Experimental studies have shown that the middle third of the flow curve has a substantially linear relationship with exhaled volume which corresponds to the case when the product of compliance and resistance is a constant.

The software of the apparatus can integrate the recorded flow readings to volume, and plot flow against volume. When flow is not turbulent, this relationship is a straight line, with the slope being the time constant. The first and last parts of the flow/volume curve are often turbulent, and the central, straight portion of the curve can be selected to simplify the necessary calculations. This can be done visually, using a graphic display of the flow/time curve, or automatically.

If increasing intra-thoracic pressure does not cause any increase in flow, then the rate of increase of $R_d$ must be equal to the rate of increase of intra-thoracic pressure. In this case, control over air flow is determined by lung compliance $C_l$ and $R_u$. The product $R_u C_l$ is the time constant of the lung for forced expiration. This is a valuable index of lung function, being linearly related to the severity of obstructive lung diseases such as asthma and emphysema, and restrictive diseases such as sarcoidosis.

In the passive expiratory mode, the invention operates by recording time constant curves (preferably sigh curves or expiratory curves under anaesthesia), with two different known resistance values in the expiratory circuit. In a "Monitor" mode, used during anaesthesia, a reading of $C_{lt} \times R_{aw}$ is provided, which is updated every minute. In a "Measure" mode, $R_{aw}$ and $C_{lt}$ measurements are displayed separately. The software incorporated in the apparatus checks the measurements until the discrepancy between successive measurements is less than 10%. The measured results are then displayed.

In the forced expiratory mode, $C_l \times R_u$ is measured. This reading is mainly useful in field work and at outpatient clinics, for example, where quick results are required for numerous patients.

The described method and apparatus allow relatively quick and accurate measurements to be made of a subject's airway resistance and lung and thorax compliance, without laborious and uncomfortable procedures. The apparatus can be made conveniently small and portable for use in the field, or in operating theatres.

I claim:

1. A method of monitoring lung function comprising the steps of:
   (a) connecting a pneumotach in series with a subject's airway;
   (b) taking a plurality of first airway pressure readings upstream and downstream of a first resistance element in the pneumotach;
   (c) inserting or removing a second resistance element in the pneumotach, wherein said first and second resistance elements create a total resistance, so that the total resistance in the subject's airway is changed;
   (d) taking a plurality of second airway pressure readings upstream and downstream of the first resistance elements in the pneumotach;
   (e) processing the plurality of first and second pressure readings to calculate respective first and second characteristic flow curves for the subject's airway;
   (f) deriving first and second time constants from the first and second flow curves;
   (g) calculating values of lung compliance and airway resistance for the subject from the first and second time constants.

2. A method according to claim 1 wherein the first and second airway flow curves are curves of air flow against time, from which the first and second time constants can be derived.

3. A method according to claim 2 wherein the time constants are calculated from a relationship $$t = \frac{t_2 - t1}{L \log V_1 - L \log V_2}$$

where $t_1$ and $t_2$ are start and end times for the first and second airway flow curves and $V_1$ and $V_2$ are corresponding lung volumes.

4. A method according to claim 3 wherein a lung and thorax compliance $C_{lt}$ and an airway resistance $R_{aw}$ are calculated from a relationship $t=R_{aw}C_{lt}$.

5. A method according to claim 2 wherein the time constants are derived from a slope of a flow/volume expiration curve.

6. Pneumotach apparatus for monitoring lung function in a subject's airway comprising:

(a) a body defining a conduit therein for connection in series with the subject's airway;

(b) a first resistance element in the conduit;

(c) first and second ports in the body in communication with the conduit on either side of the first resistance element; and (d) a second resistance element movable between an operative position in the conduit in which it increases a total resistance to gas flow in the conduit, and an inoperative position in which it does not substantially affect gas flow in the conduit, wherein the second resistance element is housed releasably in a slot in the body which intersects the conduit.

7. Pneumotach apparatus according to claim 6 wherein the first and second resistance elements are perforated plates with a predetermined effective aperture size.

8. Pneumotach apparatus according to claim 6 wherein the second resistance element is removably insertable into the body.

9. Pneumotach apparatus according to claim 6 wherein the first and second ports in the body are connectable to respective pressure sensors.

10. Pneumotach apparatus according to claim 6 further comprising:

(e) a pressure sensor housed within the body in or adjacent to the first and second ports.

11. Pneumotach apparatus according to claim 6 further comprising:

(e) first and second pressure sensors in communication with the first and second ports in the body and arranged to generate respective output signals corresponding to respective pressure readings; and (f) processing means for receiving first and second sets of output signals from the sensors, corresponding to pressure readings with the second resistance means in the inoperative and operative positions; for calculating first and second characteristic flow curves for the subject's airway; for deriving first and second time constants from the first and second flow curves; and for calculating values of lung compliance and airway resistance therefrom.

12. Pneumotach apparatus according to claim 11 wherein the pressure sensors are arranged to measure the pressure differential across the first resistance element, from which measurement of an airflow in the conduit can be calculated.

13. Apparatus for monitoring lung function according to claim 11 further including indicator means for displaying one or more measured or calculated values.

* * * * *